United States Patent [19]

Hunt

[11] Patent Number: 4,612,370
[45] Date of Patent: Sep. 16, 1986

[54] LIPID-SACCHARIDE REACTION PRODUCTS

[75] Inventor: C. Anthony Hunt, San Francisco, Calif.

[73] Assignee: The Regents of the University of California, Berkeley, Calif.

[21] Appl. No.: 558,847

[22] Filed: Dec. 7, 1983

Related U.S. Application Data

[62] Division of Ser. No. 364,919, Apr. 2, 1982, Pat. No. 4,425,334.

[51] Int. Cl.$^4$ .................. C07J 17/00; C07H 11/04
[52] U.S. Cl. ........................... 536/5; 536/18.2; 536/112; 536/117
[58] Field of Search ............... 424/180, 182; 536/5, 536/117, 6.2, 112, 18.2

[56] References Cited

U.S. PATENT DOCUMENTS

| | | | |
|---|---|---|---|
| 3,887,698 | 6/1975 | McConnell et al. | 424/12 |
| 4,078,052 | 3/1978 | Papahadjopoulos | 424/36 |
| 4,089,801 | 5/1978 | Schneider | 252/316 |
| 4,101,652 | 7/1978 | Bonati | 536/5 |
| 4,133,874 | 1/1979 | Miller et al. | 424/38 |
| 4,188,379 | 2/1980 | Pegel | 536/5 |
| 4,192,869 | 3/1980 | Nicolau et al. | 424/199 |
| 4,193,983 | 3/1980 | Ullman et al. | 424/12 |
| 4,217,344 | 8/1980 | Vanlerberghe et al. | 424/60 |
| 4,224,179 | 9/1980 | Schneider | 252/316 |
| 4,229,360 | 10/1980 | Schneider | 260/403 |
| 4,235,871 | 11/1980 | Papahadjopoulos | 424/19 |
| 4,241,046 | 12/1980 | Papahadjopoulos | 424/19 |
| 4,296,233 | 10/1981 | Enomoto et al. | 536/5 |
| 4,301,152 | 11/1981 | Ponpipom | 536/5 |
| 4,419,348 | 12/1983 | Rahman et al. | 424/180 |
| 4,461,762 | 7/1984 | Malinow | 424/182 |

OTHER PUBLICATIONS

Gregoriadis, "Febs Letters", vol. 36, No. 3, 11/73, pp. 292-296.
Papahadjopoulos et al., "Biochimica et Biophysica Acta.", 363, 1974, pp. 404-418.
Hunt et al., "Int. Jour. Pharmaceutics", vol. 8, 1981, pp. 101-110.
Bosworth et al., "Jour. Pharmaceutical Sciences", vol. 71, No. 7, 1982, pp. 806-812.
Hunt et al, "Biochem. Biophys. Acta.", vol. 719, 1982, pp. 450-463.
Hunt et al, "Science", vol. 230, 1985, pp. 1165-1168.

Primary Examiner—Johnnie R. Brown
Attorney, Agent, or Firm—Phillips, Moore, Lempio & Finley

[57] ABSTRACT

Functional oxygen transport systems (OTS) have been devised which may serve as temporary blood substitutes in the circulatory system. The OTS comprises pure crystalline hemoglobin dissolved in an aqueous solution and encapsulated within a complex lipid and carbohydrate modified lipid phase. The hemoglobin encapsulated inner aqueous phase and the encapsulating lipid phase are dispensed in an outer isotonic aqueous phase to form a suspension of the multiple water-in-oil-in water emulsion type. The emulsion is suitable to transfusion into the circulatory system to assist in oxygen transport. The carbohydrate modified lipids are included in the lipid phase to "mask" the OTS from the tissue binding and take up by the reticuloendothelial system. The OTS are also suitable for use as calibrating fluids in gas analysis apparatus.

1 Claim, No Drawings

LIPID-SACCHARIDE REACTION PRODUCTS

This is a division of Ser. No. 364,919, filed Apr. 2, 1982, now U.S. Pat. No. 4,425,334.

DESCRIPTION

1. Field of the Invention

This invention relates to the production and use of oxygen transport systems that may be used in living mammalian species for the purposes of supplying oxygen through the circulatory system, as a supplement to, or as a temporary replacement for hemoglobin carrying corpuscles. The oxygen transport system comprises a complex water-oil-water emulsion wherein a solution containing pure hemoglobin is trapped in a lipid phase which in turn is emulsified or suspended in an aqueous, physiologically acceptable isotonic external phase.

The government has rights to this invention pursuant to Contract No. DAMD17-79-C-9045 awarded by the U.S. Army Medical Research and Development Command.

2. Background of the Invention

A number of proposals have been advanced for oxygen transport systems as a temporary substitute, or partial substitute for the natural oxygen carrying red blood cells in mammals. Temporary disfunction, violent trauma and other mishaps or accidents sometimes require a substitute or at least partial substitute for the blood cells. In many instances whole blood is unavailable, or if available, may be of the incorrect type. Plasma, if available, aids in maintaining circulatory volume, but it is devoid of any oxygen carrying component. Thus the development of artificial resuscitative fluids have been investigated for a number of years, but to date no universally acceptable product has yet been approved.

Basically an artificial resuscitative fluid should have the following properties to be feasible:

It should function for at least several hours as well as normal blood having a hematocrit of about 15–20%.

It should not be toxic.

It should be sterile and pyrogen free.

It should be free of any antigens, i.e., it should not activate the body's immune system; nor should it require any blood typing analysis.

It should have a reasonable "shelf-life" at least as long as, or longer than, fresh whole blood.

Many different approaches have been made in providing a viable oxygen transport system. One generally promising approach utilizes fluorocarbon emulsions. Such emulsions are capable dissolving oxygen in the non-aqueous phase, and under the proper conditions, releasing it to the surrounding tissues. Although fluorocarbon emulsions are themselves biologically acceptable from an antigen-free standpoint, they are subject to removal from circulation by the reticuloendothelial systme (RES) which is part of the body's immune defense mechanism. Inert colloidals such as fluorocarbon emulsions, if removed with facility by the reticuloendothelial system may produce a "blockade" of the RES. More specifically, RES cells function to remove bacteria, viruses and many other particulates from the circulation. If the RES cells are overloaded by a large dose of particulates, as would be the case in the infusion of a fluorocarbon emulsion, they "shut down" and temporarily cease to function, or function at greatly reduced capacity. In this state, the body is quite susceptible to infection. Many emulsions are known to cause this "RES blockade".

In another approach, liposome technology has been employed. Liposomes are small vesicles comprising one or more concentric lipid bilayer spheres enclosing an interior space or spaces. These spaces may contain any water soluble active agent, which will be transported in the liposomes and released therefrom under certain conditions. In the present instance, oxygen transport systems comprising liposomes encapsulating the normal hemoglobin containing aqueous contents of red cells have been utilized as artificial resuscitative fluids. However, liposomes having a resemblance to emulsions, are also primarily removed from circulation by the reticuloendothelial system. Thus the liposome approach is subject to many of the problems associated with fluorocarbon emulsions.

In addition, hemoglobin is a relatively fragile material which is easily degraded by elevated temperatures, contact with oxidizing and reducing agents, and any severe handling procedures. Any denaturization of hemoglobin itself, or the presence of hemoglobin degradation products are undesirable in an artificial oxygen transport system. Such products are also readily taken up by the RES, since they tend to be antigenic and exhibit immunogenic properties. While the total content of natural red blood cells would also appear as being ideal for inclusion in an artificial oxygen transport system, quite the opposite is the case. The various proteins and enzymes within the red blood cell can become incorporated into any lipid membrane into which the cell contents are placed. These proteins and enzymes induce antigenic, immunogenic, and adverse blood clotting reactions. Thus oxygen transport systems incorporating hemoglobin degradation products, or proteins and enzymes from natural red blood cells are rapidly cleared from the circulatory system. The amount of the oxygen transport system in circulation therefore quickly decreases and the oxygen transport effectiveness disappears. At the same time, the rapid uptake by the RES, may produce "RES blockade" with its concomitant undesirable effects on the body.

An artifical oxygen transport systems has now been devised that overcomes the problem set forth above.

BRIEF DESCRIPTION OF THE INVENTION

This invention presents an artificial oxygen transport system that is free from antigenic and immunogenic components; that incorporates components that "mask" the system from the body's RES and thereby permits extended circulation to provide relatively long term transport of oxygen throughout the body.

The oxygen transport system (OTS) of the invention comprises a complex water-oil-water emulsion (sometimes referred to as a multiple emulsion), wherein a pure, truly stroma-free, crystallized hemoglobin aqueous solution comprises the inner water phase; a carefully selected lipid mixture including "masking" lipids comprises the middle oil phase, and an isotonic aqueous solution comprises the outer water phase. The inner aqueous phase and the surrounding oil phase comprises the essential "working" components of the oxygen transport system. The external aqueous phase comprises the liquid medium in which the working OTS is transfused or injected into the circulatory system.

The present invention also presents methods for producing the artificial OTS. These methods succeed in producing the OTS without degrading the pure hemoglobin or producing undesirable antigens or immunogens, or degrading the oxygen carrying capacity of the hemoglobin.

With more particularity, the oxygen transport system is a complex water-oil-water emulsion. The oil phase includes naturally occuring phospholipids of the type which form "membranes"; and, in addition, a synthetic "masking" lipid that minimizes tissue binding and RES take up of the emulsion particulates. The oil phase consists of a mixture of the noted lipid or lipid derived materials. It functions as do natural membranes and those of microcapsules, to separate and isolate the internal aqueous phase from the outer, suspending aqueous phase. The internal water phase consists of a hemoglobin solution constituting stroma-free crystallized hemoglobin, a glycerate or phosphate, a buffer (pH about 7.4), and dissolved solutes to allow the final solution to become isoosmolar with plasma. The external water or aqueous phase consists of a buffer (pH 7.4) isotonic solution.

In the present invention, the two internal emulsion phases i.e., the intermediate oil phase and the internal water phase, effectively constitute "capsules" wherein the oil phase encloses the oxygen bearing hemogloblin in the interior water phase. The oil phase and the enclosed water phase constitute a synthetic blood cell wherein the dissolved crystalline hemoglobin may pick up oxygen across the pulmonary membranes and effectively transport the same to other portions of the circulatory system.

While the oil-water phases effectively mimic red blood cells, for the purposes of the present invention, it is not desirable to simply incorporate glycoproteins and/or glycolipids normally found in red blood cells into the oil phase and expect the resulting oxygen transport system to avoid interaction with tissues. These glycoproteins and glycolipids which constitute the outer membrane of natural red blood cells are a primary basis for "blood type" and their inclusion into a universal oxygen transport system would be undesirable. On the other hand, these carbohydrates do act as a buffer or cushion to prevent direct contact of the red blood cell or platelet surface with tissue cell surfaces.

While inclusion of the naturally occuring glycoproteins and/or glycolipids, in a universal transport system is undesirable as noted above, it is desirable to prevent direct contact of the OTS with the RES tissue cell surfaces. This dilemma is solved in the present invention by the inclusion in the oil phase of a masking lipid which serves to "hid" the OTS from the RES.

Theoretically, the "masking effect" could be achieved by covering the OTS surface with an inert carbohydrate such as sucrose, dextran or inulin, which are known to have little or no affinity for tissues. However, since such carbohydrates have little affinity for biomembranes they also do not bind to the other lipids present in the oil phase of the OTS. Therefore to have such inert carbohydrates permanently protecting the OTS the present invention couples or covalently attaches such carbohydrates directly to lipid components in the oil phase. These carbohydrate-lipid molecules may be found by either covalently attaching the carbohydrate directly to the pre-formed particle surface, or alternatively, by synthesizing the carbohydrate-containing lipid and then incorporating it into the membrane phase during the formation of the OTS. The latter technique is preferred in the present invention.

In any event, the "masking" carbohydrate-containing lipid is incorporated into the oil phase of the OTS along with other lipids to form the OTS membrane and to effectively "mask" the OTS from the RES system of the body.

It is therefore an object of the invention to provide a functional synthetic oxygen transport system.

It is another object of the invention to provide a functional oxygen transport system comprising a water-oil-water emulsion wherein crystalline hemoglobin is dissolved in the inner water phase.

It is still another object of the invention to provide a functional oxygen transport system comprising a water-oil-water emulsion wherein crystalline hemoglobin is dissolved in the inner water phase and the oil phase includes physiologically acceptable lipids and additionally added amounts of chemically modified lipid which serve to "mask" the oxygen transport components from tissue binding and/or take up by the reticuloendothelial system of the body.

It is still another object of the invention to provide a physiologically acceptable oxygen transport system that may be circulated throughout the vascular system for extended periods of time.

Other objects and advantages of the invention will be apparent from a review of the following description and the claims appended hereto.

DETAILED DESCRIPTION OF THE INVENTION

The oxygen transport system of the invention comprises, as its essential components, truly stroma-free, crystalline hemoglobin that is dissolved in an aqueous solution which is, in turn, encapsulated, as an internal aqueous phase within a lipid or oil phase to comprise a water-in-oil emulsion or microcapsule. For purposes of delivering the encapsulated pure hemoglobin into the circulatory system, the water-in-oil emulsion is, in turn, suspended in an external isotonic aqueous phase. The oxygen transport system (OTS) when prepared for injection, or transfusion, into the body, or use as a blood standard therefore comprises a water-oil-water emulsion with an aqeuous solution of crystalline hemoglobin comprising the inner water phase. The oil phase comprises naturally occurring lipids, including phospholipids and, additionally, modified lipids that serve to protect the lipid encapsulated hemoglobin from tissue binding or take up by the reticuloendothehal system. The outer water phase comprises an isotonic aqueous solution that acts as the carrier for the lipid encapsulated hemoglobin when such components are to be injected or transfused into the body.

It is important that the hemoglobin be entirely free from portein components which could induce an immune reaction. It should be stroma-free, and in addition, it must be handled very cautiously during preparation of the OTS to avoid any denaturization or conversion to such products as methemoglobin, myoglobin, and globin, all of which are undesirable because of their physiological properties or potential antigenicity and interference with oxygen transport. The hemoglobin for use in the OTS is therefore produced as a pure crystalline product by the procedure of DeVenuto et al. as set forth in J. Lab. Clin. Med., 80, #3, pages 509–516 (1977), which procedure is incorporated herein by reference.

The pure crystalline hemoglobin is dissolved in water to produce an aqueous solution thereof which is at least 15% by weight hemoglobin. In order to stabilize the hemoglobin solution and to make the aqueous phase isoosmolar with normal blood, about 1 to 2 moles of 2,3-disphosphoglycerate or about 0.5 to 1 mole of inositol hexaphosphate per mole of hemoglobin; as well as 20-30 miliosmolar pH 7.4 phosphate buffer. Sufficient dissolved solutes, such as dextrose, may also be included when it is desired to make the final solution isoosmolar with the blood plasma before the microencapsulationprocess begins.

Such aqueous hemoglobin solution contains no blood cell derived proteins other than hemoglobin itself, and has a useful life approximating that of whole fresh blood, i.e., approximately three weeks.

The oil phase in which the inner hemoglobin aqueous phase is enclosed, consists of naturally occurring lipids such as phosphatidylcholine, phosphatidic acid, cholesterol, and α-tocopheral. Such lipids are usually present in admixture: however, α-tocopheral is especially important as an antioxidant to prevent autooxidation of both the hemoglobin and the lipids. Should oxidation of the lipids occur, the resulting products, can themselves denature the hemoglobin, and/or become antigenic to the body. Should oxidation of the hemoglobin occur, the resulting product is methemoglobin which does not bind oxygen. Thus an antioxidant such as α-tocopherol is always included in the oil phase of the OTS.

In addition to the naturally occurring lipids, the oil phase also includes "masking" lipids which minimize the tissue binding properties of the emulsion microparticulates. Thus uptake by the RES is reduced and the useful lifetime of the OTS in the circulatory system is prolonged.

The "masking" lipids consist of the reaction product of biologically inert carbohydrates such as sucrose, dextran, inulin, etc. with naturally occurring lipids such as phosphatidyl ethanolamine. The preparation of some "masking" lipids and their incorporation into the membrane phase will be noted in some examples set forth below.

The "masking" lipids may either be prepared as a separate product and thereafter be incorporated into the membrane phase; or alternately, be produced directly by carbohydrate reaction with the pre-formed particles. The former method is usually preferred. In any event, the "masking" lipids may comprise from about 1 to 50 percent by weight of the oil phase.

With more particularity, a functional masking lipid consists of three parts i.e., a lipid or phospholipid base unit; an oligosaccharide or polysaccharide; and a terminating mono- or disaccharide unit. The saccharide terminal unit normally comprises a portion of the oligosaccharide or polysaccharide. An example of such masking lipid is the reaction product of melezitose and phosphatidylethanolamine.

The oligosaccharide unit should be nonreducing once attached to the lipid or phospholipid base unit. Generally the larger the obligosaccharides are preferred since they provide more protection per masking lipid and function as a better "spacer". The terminal saccharide unit should be nonreducing. Further, it should not be an amino sugar nor should it be either galactose or mannose. Most preferably, such terminal saccharide unit should be either glucose or fructose in a nonreducing form. The lipid or phospholipid base unit should be either a natural lipid or it should be a metabolizable and non-toxic in its unreacted form. It should also have a functional group for attachment to the oligosaccharide and it should be easily incorporated into the OTS membrane without significant membrane destablization. Phosphatidylethanolamine ideally satisfies these requirements although other naturally occurring lipids may be used. Examples of the preparation of typical "masking" lipids will be set forth in the examples below.

The external aqueous phase of the OTS consists of a buffer isotonic solution, ideally at a pH of 7.4. The external aqueous phase serves as the liquid medium to carry the OTS particulates into the circulatory system. The external aqueous phase may be any of the standard buffered saline solutions which are commonly utilized for medicinal purposes.

There are a number of procedures which have been developed for the preparation of the OTS suspension. Such procedures are noted above, must not be so severe as to degrade the crystalline hemoglobin solution. The procedures must also be selected so as to effectively suspend of the hemoglobin aqueous solution within the lipid oil phase. The following procedures have been developed to produce the OTS without denaturing the hemoglobin:

PREPARATION PROCEDURE A

The desired phospholipids including the antioxidant, α-tocopherol and the masking lipids are first dissolved in a volume of an organic solvent such as an ether (diethyl and/or propylether). Sufficient halocarbon (Freons) having a vapor pressure as close to that of the ether as possible e.g., trifluoro-trichloroethane is added to the ether solution until the density of the mixed lipid-ether-halocarbon solution matches that of the aqueous hemoglobin phase which is to be encapsulated. The lipid-ether-halocarbon solution is then added to the previously prepared aqueous solution of hemoglobin and the other aqueous components as noted above. The mixed oil-water phases are then shaken very rapidly to form a multiple emulsion of the oil-water-oil type. Sonication must not be used since it will partially denature the hemoglobin. Emulsification should be by a technique which minimizes the amount of solution-gas phase contact. In this regard it is advantageous to utilize an inert gas, such as nitrogen or argon as the gas phase over the liquid phases.

Shaking of the oil and aqueous phases is continued to ensure complete emulsification wherein a multiple oil-water-oil emulsion is formed in which the particle sizes are approximately 2.0 micometers in diameter or less.

Once the oil-water-oil emulsion is formed the organic solvents are then removed under a low vacuum while the emulsion is maintained at a constant temperature. As the solvents are removed the viscosity of the entire suspension increases. Evaporation of the organic solvent components is continued with vigorous shaking until less than 1% thereof remains and viscosity radically increases. This increase is the result of an emulsion phase inversion from the oil-water-oil condition into the water-oil-water emulsion.

After inversion into the water-oil-water emulsion occurs, the resulting aqueous suspension is then extruded through a Nucleopore membrane, e.g. 0.4 micrometer diameter pore-size.

To the resulting extruded aqueous suspension is added four times the volume of a isoosmolar buffer (pH 7.4) having a molarity identical to the original aqueous phase. The resulting suspension is then centrifuged to separate the OTS particles from the suspending aqueous hemoglobin solution. The upper liquid phase is then removed from the packed OTS. Subsequently, the same volume of aqueous buffer is added to the packed OTS's which are resuspended and then again centrifuged. The buffer is once again removed and replaced with a final volume of aqueous buffer and the OTS's are resuspended to give the final product.

The addition and removal of successive volumes of the aqueous buffer serves to eliminate any unencapsulated hemoglobin solution from the suspension. It may also be used to separate hemoglobin "rich" from hemoglobin "poor" particles, the former having the higher density and greatest tendancy for centrifugal separation, the latter being relatively less useful as an OTS. The resultant final suspension therefor comprises the hemoglobin free external aqueous phase, the lipid, or oil, middle phase and the encapsulated inner hemoglobin aqueous phase.

In a variation the suspension produced after extrusion may be added to an appropriate gel-exclusion column wherein the free hemoglobin is separated from the OTS particles. Suitable amounts of the external hemoglobin free aqueous buffer solution is then added to the eluted OTS particles.

In another variation, once the initial OTS suspension is produced as noted above, the free hemoglobin which has been unencapsulated within the oil phase is filtered from the OTS particles using the technique of constant volume filtration and an appropriate membrane filter.

In any event, the final water-oil-water emulsion is then ready for use, or may be stored under refrigeration.

A somewhat different procedure may also be utilized for the preparation of the OTS. In this procedure the initial oil-water-oil emulsion is produced exactly as in the previous procedure. However, upon formation of the oil-water-oil emulsion, the temperature is rapidly lowered to $-76°$ C. At these freezing temperatures the water phase is quickly converted from a liquid into a frozen solid. At the same time, because of its much lower freezing piont, the oil phase remains liquid. The temperature must be lowered very rapidly in order to avoid formation of any "large" ice crystals which would damage the hemoglobin. In any event, the freezing produces a solid in liquid suspension.

While maintaining the aqueous phase frozen, the liquid non-aqueous phase is subjected to a vacuum to remove the organic solvents while keeping the temperature below $-15°$ C. When less than 1% of the solvents remain the temperature is thereupon rapidly increased to room temperature while shaking or rotating. This process inverts the emulsion, producing the desired W/O/W emulsion. The resulting aqueous suspension is then forced through a Nucleopore membrane as noted in the previous procedure.

Successive volumes of 7.4 buffer solution are then added and decanted in order to remove any unencapsulated hemoglobin. The procedure is the same as that previously noted i.e., the aqueous buffer is added to the OTS's. The solution is centrifuged to separate the OTS's and the aqueous buffer phase is then decanted and resuspended with additional amounts of the aqueous buffer etc. The resulting product is the external hemoglobin free aqueous phase at pH 7.4; the intermediate lipid oil phase; and the internal encapsulated hemoglobin aqueous phase. The resulting product is identical with that produced in the earlier noted procedures.

As briefly noted above, the masking lipids may be separately prepared, and then added to the other lipids comprising the oil phase of the OTS. Alternately, the masking lipids may be formed in situ by carbohydrate reaction with a portion of the lipids already forming the oil phase of the OTS. In the Examples set forth below there is presented two examples of each method of incorporating the masking lipids independent of oil phase.

The first two examples describe the preparation of masking lipids separately from the OTS. The second two examples describe the properation of masking lipids by direct reaction of the carbohydrate with lipids already present in the formed OTS.

EXAMPLE A-1

The preparation of raffinose-phosphatidylethanolamine (PE)

This procedure is based on the procedure of J. Van Zile et al. (*J. Bio. Chem.*, 254(9), 3547–3553, 1979).

Raffinaldehyde is generated from raffinose (a galactose-sucrose trisaccharide) using galactose oxidase.

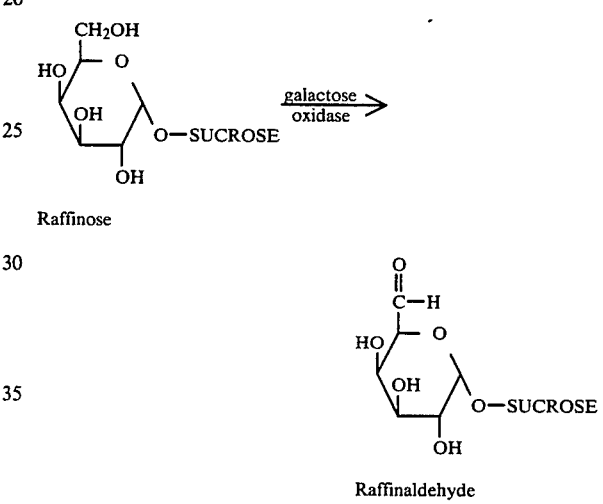

Raffinose

Raffinaldehyde

To a pH 7 solution of raffinose, 5 mol/ml, add 20 units/ml of galactose oxidase, 130 units of catalase and incubate at 37° for 4 hours. Then separate the raffinaldehyde and unreacted raffinose from the enzymes on a Sephadex column using distilled water as the eluant. The triose peak, collected from the column, is then freeze dried, and dissolved in tetrahydrofuran. For each mol of original raffinose, 0.3 mol of PE is added along with 0.3 mg of NaBH$_3$CN (dilute and heat if precipitation occurs). Reaction is continued at 50° for 8 hours, and the reaction mixture is then reduced to dryness under vacuum (if unreacted PE 5%, repeat). The residue is then dissolved in minimum amount of warm methanol. The above reaction is a classical Shiff's base formation and reduction to give:

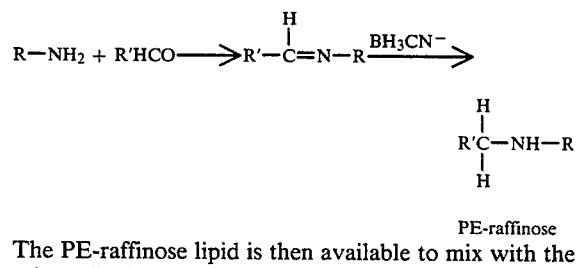

PE-raffinose

The PE-raffinose lipid is then available to mix with the other oil phase lipids to form the OTS membrane as previously described.

PE-malabiose may be obtained in essentially the same way by simply substituting glucose oxidase for galactose oxidase in the above procedure. Malabiose is a glucose-sucrose trisaccharide.

EXAMPLE A2

The preparation of sucrose-PE

This synthesis is based on standard synthetic procedures and is outlined below:

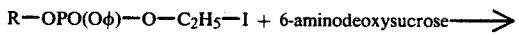

R—OPO(O$\phi$)—O—C$_2$H$_5$—I + 6-aminodeoxysucrose ———>
 I                                II

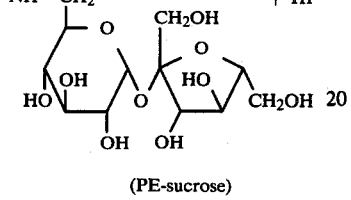

(PE-sucrose)

In the above reaction R =

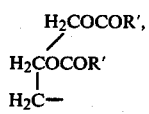

where R'COOH = fatty acid

To prepare compound (I):

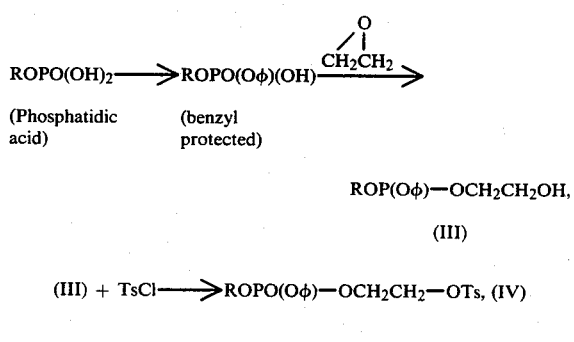

to prepare compound (II):

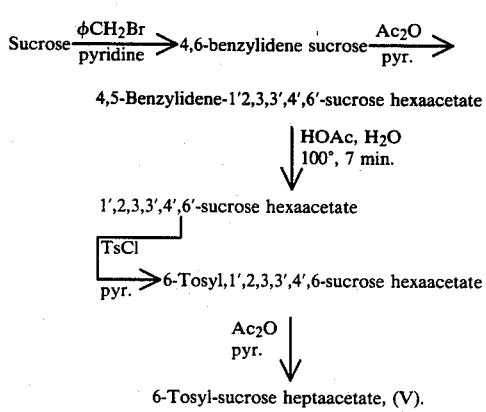

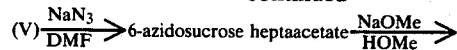

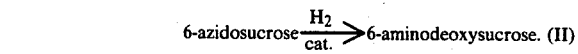

The PE-sucrose reaction product is then incorporated into the OTS along with the other lipid components as noted above.

EXAMPLE B1

The preparation of PE-inulin in situ in the OTS oil phase

A saturated solution of insulin is prepared at pH 5.0, 0.15M acetate buffer. 10 ml of a 0.1M NaIO$_4$ (pH 5.0) solution is added to each 100 ml of inulin solution and allowed to react for one hour in the dark. The mixture is then dialyzed for two hours against, or against an excess of, the reducing solution, which consists of 20 mM H$_3$BO$_3$, 20 mM Na$_2$B$_4$O$_7$ and 100 mM NaCl adjusted to pH 8.5. After dialysis this solution is mixed, ml for ml, with the preformed OTS solution, where the OTS membrane contains a specific amount of phosphatidyl ethanolamine as the substrate for subsequent carbohydrate reaction, and where the lipid concentration has been adjusted to 10 m mol/L in pH=8.5 borate buffer. After 12 hrs. at 20° NaBH$_3$ is added to produce final concentration of 0.3 g/L. After 1 hr. the OTS is separated by centrifugation and washed twice with isotonic phosphate (pH 7.4) buffer. This procedure attaches partially oxidized inulin to 10 to 50% of the oil phase surface PE.

EXAMPLE B2

A preparation of PE-dextran in situ

The procedure for preparation of PE-dextran is the same as that for Example B1 above. Unlike inulin, soluble dextran must be purified prior to the synthesis to obtain the desired molecular weight fraction. For example, the 4000–8000 MW fraction, using Sephedex G-10 chromatography, is first isolated. Preparation is then the same as above in Example B-1. The yield is approximately the same for either methods B1 or B2.

In Vitro Testing of OTS

Several variations of/OTS have been tested to determine their P$_{50}$, Hill number, n, and hepatic clearance, among other parameters. For convenience the final composition of each/OTS may be indicated by the relative moles of each component present. Various types of OTS for transfusion are designated according to the final preparation procedure. For purposes of identification the OTS are designated as various types.

Following extrusion, if the internal (entrapped) and external aqueous phases are kept at pH 7.4, 30 mosm, then these OTS are designated type A. In type B, the internal and external aqueous phases are at pH 7.4 and 300 mosm, due to 30 mosm phosphate buffer and 270 mosm dextrose; type B OTS are isoosmatic with plasma. Type C are also at pH 7.4 and 300 mosm, but the buffer is composed only of phosphate salts and, as a result, has a much higher ionic strength. Type D are initially the same as type A through the extrusion step, however, before dialysis, the external osmolarity is slowly adjusted to 300 mosm (without rupture of the OTS). Following dialysis of excess unencapsulated hemoglobin if the higher density, hemoglobin-rich OTS are separated rrom all other OTS by centrifugation at 6000 g for 15 min (centrifugation is adjusted such that ½ of the total OTS volume is recovered as the centrifugate), then these OTS are designated with R (for hemoglobin "rich"), e.g. type CR. Results of in vitro testing of various OTS are listed in Table 1.

In Vivo Testing

In vivo testing was designed to test either the survival time of OTS in the circulation of mice or evaluate the ability of OTS to function in rats as an oxygen transport system. Using procedures in accordance with the publication of De Venito et al. in Transfusion 17, No. 6, 555–561 (1977) incorporated herein by reference, and based on the results of these same studies, a reasonable measure of relative circulation retention is revealed as the percent of an injected OTS dose remaining per ml of blood. For these studies a small amount of $^{14}$C-inulin was included as a valid marker, as in the above noted procedure.

In the transfusion studies, the same procedures were followed. To test long-term survival, rats were transfused with OTS suspended in Ringers solution. For the 250–300 g rats used, approximately 5 ml of blood was withdrawn and replaced by 5 ml of OTS suspension. After approximately 3–5 min this process is repeated, and repeated again for a total of up to 10 withdrawals/additions. After a designated period the process is repeated with whole rat blood. When this procedure was carried out using only the Ringers solution, approximately 50% of the rats died before the 10th withdrawal/addition. The remainder died between the 9th withdrawal/addition and 10 min. following the 10th withdrawal/addition.

TABLE 1

| CASE | [1]TYPE OF SYSTEM (CONTROL OR OTS) | | [2]TYPE OF MASKING LIPID | g % Hb used | $P_{50}$ | n | [3]g % Hb final | [4]Hepatic ER(%) |
|---|---|---|---|---|---|---|---|---|
| 1 | | Hb alone | — | 6 | 12 | 1.9 | 6.3 | — |
| 2 | | Hb alone | — | 12 | 13.4 | 2.4 | 12.4 | — |
| 3 | | Hb alone | — | 18 | 16.8 | 2.5 | 18.3 | — |
| 4 | OTS: | TYPE-AR | PE-sucrose (11%) | 6 | 18.0 | 1.9 | 4.85 | 5 (compare,12)[6] |
| 5 | | TYPE-AR | PE-sucrose (11%) | 12 | 20.7 | 2.2 | 9.63 | 5 (compare,12)[6] |
| 6 | | TYPE-AR | PE-sucrose (11%) | 18 | 24.4 | 2.3 | 14.2 | — |
| 7 | | TYPE-AR | PE-sucrose (20%) | 12 | 18.8 | 2.0 | 8.6 | 3 (compare,12)[6] |
| 8 | | TYPE-AR | PE-sucrose (20%) | 18 | 22.7 | 2.3 | 12.6 | — |
| 9 | | TYPE-AR | PE-sucrose[5](20%) | 12 | 21.1 | 2.3 | 9.7 | — |
| 10 | | TYPE-AR | PE-sucrose[5](20%) | 18 | 23.7 | 2.4 | 14.2 | — |
| 11 | | TYPE-A | PC (20%) | 8.3 | 22.1 | 1.8 | 3.6 | 20 |
| 12 | | TYPE-AR | PC (20%) | 8.3 | 22.1 | 1.8 | 5.2 | 20 |
| 13 | | TYPE-A(1HP) | PC (20%) | 8.3 | 25.7 | 1.0 | 3.3 | 21 |
| 14 | | TYPE-A | PE-raffinose (10%) | 8.3 | 23.2 | 2.0 | 4.4 | 5 (compare,11)[6] |
| 15 | | TYPE-AR | PE-raffinose (10%) | 8.3 | 23.2 | 1.9 | 5.7 | — |
| 16 | | TYPE-A(1HP) | PE-raffinose (10%) | 8.3 | 25.5 | 1.1 | 4.5 | — |
| 17 | | TYPE-C | PC (20%) | 33.0 | 20.6 | 1.8 | 8.6 | 18 |
| 18 | | TYPE-CR | PC (20%) | 33.0 | 20.6 | 1.8 | 12.3 | — |
| 19 | | TYPE-C | PE-raffinose (8%) | 33.0 | 21.3 | 1.8 | 9.2 | 3 (compare,17)[6] |
| 20 | | TYPE-CR | PE-raffinose (8%) | 33.0 | 21.3 | 1.8 | 15.1 | — |
| 21 | | TYPE-B | PC (20%) | 8.3 | 22.9 | 1.8 | 6.1 | — |
| 22 | | TYPE-BR | PC (20%) | 8.3 | 22.9 | 1.8 | 8.8 | 30 |
| 23 | | TYPE-BR | PE-dextran | 8.3 | 23.0 | 1.8 | 9.1 | 11 (compare,22)[6] |
| 24 | | TYPE-C | PC (20%) | 8.3 | 21.2 | 1.9 | 2.1 | — |
| 25 | | TYPE-CR | PC (20%) | 8.3 | 21.2 | 1.9 | 2.1 | — |
| 26 | | TYPE-DR | PC (20%) | 15.3 | 23.1 | 2.1 | 12.3 | 23 |
| 27 | | TYPE-DR | PE-inulin (3%) | 15.3 | 23.1 | 2.0 | 13.1 | — |
| 28 | | TYPE-DR | PE-dextran (10%) | 15.3 | 22.9 | 2.1 | 12.6 | 16 (compare,26)[6] |
| 29 | | TYPE-DR | PE-inulin (9%) | 16.2 | 24.1 | 2.0 | 13.6 | — |
| 30 | | TYPE-DR | PE-raffinose (20%) | 16.6 | 24.2 | 2.1 | 13.3 | 15 (compare,26)[6] |
| 31 | | TYPE-DR | PE-raffinose (30%) | 16.6 | 23.9 | 2.2 | 13.5 | 20 (compare,26)[6] | where
ML = masking lipid;
PC = phosphatidyl choline;
PA = phosphatylic acid;
CH = cholesterol; and
T = α-tocopherol.

[1]In each case the composition was ML/PC/PA/CH/T in the molar ratio x/4 − x/1/5/0.1, where the percent of ML on the surface is designated in column two. pH was 7.4. In most cases diphosphoglycerate was entrapped along with hemoglobin (Hb) in a molar ratio of 1.6:1 unless indicated otherwise. Met-Hb levels were less than 5% in all cases. Total lipid was approximately 50 moles per ml of starting Hb solution.

[2]Except for changes in the nature of the masking lipid the composition was as indicated above. Total phospholipid, including ML, was kept at 50 mol %. The percent of total phospholipid that was masking lipid on the OTS surface is indicated in parenthesis and has been estimated from the amount of ML incorporated and the average surface area of the OTS (see Pidgeon and Hunt, J. Pharm. Sci, 70(2) 173–176, 1981). Using PC as the ML increased the total amount PC in the OTS to 80% of the total phospholipid. These OTS served as controls for those with carbohydrate-containing ML.

[3]After OTS formation an aliquot was centrifuged and excess buffer removed. The resulting OTS had hematocrits of 90–100%. The g % Hb in this final suspension are based on the maximum amount of $O_2$ that could be associated.

[4]The values are the hepatic extraction ratios, ER. They are the experimentally determined % of a liposome suspension that is removed from rat liver in a single pass (using the isolated perfused rat liver system). For the OTS composition without ML, ER averages 23.5 + 4.5%. A reduction in this value was always reflected by an increase in circulation half-life using rats.

[5]For these OTS 50% of the PC was replaced by sphingomylin.

[6]The indicated values are controls; by values are reflected in longer circulation half-lives.

Table 2 below presents data on the retention times of the OTS in the circulation.

TABLE 2

RELATIVE RETENTION [1] OF OTS IN THE CIRCULATION

| NO. FROM TABLE 1 | [2]TYPE OF OTS | [3]TYPE OF Masking Lipid | [4]DOSE (mg/20 g) | % DOSE REMAINING IN BLOOD AT 4 HOURS | [5]RELATIVE INCREASE IN HALF-LIFE |
|---|---|---|---|---|---|
| #4  | AR | PE-sucrose (11%)   | 15   | 17.3 | 43× |
| #7  | AR | PE-sucrose (20%)   | 34.7 | 71.6 | 179× |
| #11 | A  | PC                 | 13.4 | 0.4 (control) | — |
| #26 | DR | PC                 | 33.4 | 2.6  | 6.5× |
| #14 | A  | PE-raffinose (10%) | 13.5 | 3.6  | 9× |
| #23 | BR | PE-dextran (5%)    | 13.7 | 5.7  | 14× |
| #29 | DR | PE-inulin (9%)     | 14.4 | 9.6  | 24× |

[1] Bolus doses of OTS were given to mice; a radio-labelled aqueous space marker was included for quantitation (Abra and Hunt, Biochem. Biophys. Acta, 666, 4013-505, 1981). The amount of Hb entrapped had little effect on OTS circulation time.
[2] See Table 1, footnote #1.
[3] See Table 1, footnote #2.
[4] This indicates the total lipid dose administered per 20 g. Mice averaged 24 g. The extravascular binding of OTS is saturable, therefore higher doses are expected to have larger 4 hr. blood retention values.
[5] For particulates such as OTS the ratio of two 4 hr. blood values is identical to the ratio of half-lives measured at the same time.

From the data above, it will be apparent that OTS having compositions in accordance with the invention offer prolonged retention in the circulatory system and improved oxygen transport over simple lipid encapsulated hemoglobin.

Other uses of the OTS will become apparent to those skilled in the art of gas transport systems. All such uses are meant to be included in the specification hereof and the claims appended hereto.

I claim:

1. A composition of matter consisting of the reaction product of a lipid or phospholipid selected from the group consisting of phosphatidyl ethanolamine, phosphatidic acid, cholesterol, and phosphatidyl alkanolamine, and a polysaccharide or oligosaccharide selected from the group consisting of sucrose, inulin, malabiose, raffinose, and dextran.

* * * * *